United States Patent

Hofmann et al.

Patent Number: 5,147,911
Date of Patent: Sep. 15, 1992

[54] COMPOSITIONS STABILIZED WITH POLY-1,3,2-OXAZAPHOSPHOLIDINES

[75] Inventors: Peter Hofmann, Basel, Switzerland; Paul A. Odorisio, Edgewater, N.J.; Glen T. Cunkle, Stamford, Conn.; Don Sabrsula, Peekskill, N.Y.

[73] Assignee: Ciba-Geigy Corporation, Ardsley, N.Y.

[21] Appl. No.: 764,022

[22] Filed: Sep. 23, 1991

Related U.S. Application Data

[62] Division of Ser. No. 572,729, Aug. 23, 1990, Pat. No. 5,075,481.

[51] Int. Cl.⁵ .......................... C08K 5/5399
[52] U.S. Cl. ........................ 524/95; 524/94; 524/97; 524/100; 524/101; 524/102; 524/131; 524/191; 524/283; 524/291; 524/343; 524/350; 252/400.21
[58] Field of Search .......... 252/400.21; 524/94, 524/95

[56] References Cited

U.S. PATENT DOCUMENTS

| | | | |
|---|---|---|---|
| 4,751,319 | 6/1988 | Odorisio et al. | 558/76 |
| 4,812,501 | 3/1989 | Odorisio et al. | 524/117 |
| 4,831,178 | 5/1989 | Odorisio et al. | 558/76 |

FOREIGN PATENT DOCUMENTS 3047443  7/1982  Fed. Rep. of Germany.

OTHER PUBLICATIONS

S. D. Pastor et al., J. Am. Chem. Soc., 110, 6547 (1988). Abstract for German 3,047,443.

Primary Examiner—Mary C. Lee
Assistant Examiner—Michael G. Ambrose
Attorney, Agent, or Firm—Luther A. R. Hall

[57] ABSTRACT

Compounds of formula I

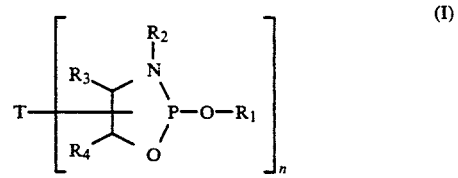

wherein n is 2-4, $R_1$ is alkyl, cycloalkyl, phenylalkyl, phenyl or a radical of formula II

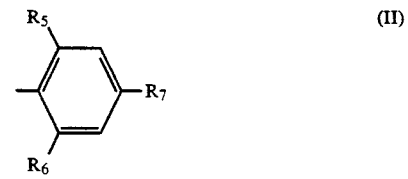

$R_2$, $R_3$ and $R_4$ are independently hydrogen, alkyl, cycloalkyl, phenylalkyl or aryl, or $R_3$ and $R_4$ together are alkyl, $R_5$ and $R_6$ are independently hydrogen, alkyl, cycloalkyl or phenylalkyl, $R_7$ is hydrogen, alkyl or a group of the formula $-(CH_2)_k COOR_8$, where k is 0-2 and $R_8$ is hydrogen or alkyl, and T is an n-valent hydrocarbon radical which may be interrupted by heteroatoms, are useful stabilizers for substrates subject to the deleterious effects of oxygen, heat and/or actinic radiation.

11 Claims, No Drawings

COMPOSITIONS STABILIZED WITH POLY-1,3,2-OXAZAPHOSPHOLIDINES

This is a divisional of Ser. No. 572,729 filed Aug. 23, 1990, now U.S. Pat. No. 5,075,481.

This invention pertains to new poly-1,3,2-oxazaphospholidines and to compositions stabilized therewith against the deleterious effects of oxygen, heat and/or actinic radiation.

BACKGROUND OF THE INVENTION

U.S. Pat. Nos. 4,751,319; 4,812,501 and 4,831,178 describe 1,3,2-oxazaphospholidine stabilizers which are peripherally related, but which are structurally quite different from the instant compounds.

The instant compounds provide excellent melt flow stabilization and excellent resistance to discoloration during processing of polymeric substrates.

OBJECTS OF THE INVENTION

One object of this invention is to provide new poly-1,3,2-oxazaphospholidine compounds which are effective stabilizers for organic materials subject to oxidative, thermal and/or actinic degradation.

A further object of this invention is to provide compositions stabilized against the deleterious effects of oxygen, heat and/or actinic radiation by containing an effective stabilizing amount of the instant poly-1,3,2-oxazaphospholidine compound.

DETAILED DISCLOSURE

The instant invention pertains to poly-1,3,2-oxazaphospholidine compounds of formula I

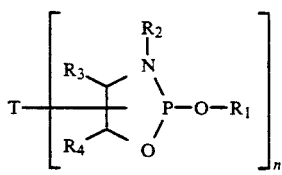

wherein
n is an integer from 2 to 4, $R_1$ is alkyl of 1 to 20 carbon atoms, cycloalkyl of 5 to 12 carbon atoms, phenylalkyl of 7 to 15 carbon atoms, said phenylalkyl substituted on the phenyl ring by one or two alkyl groups of 1 to 12 carbon atoms, aryl of 6 to 10 carbon atoms or a radical of formula II

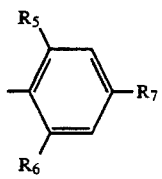

$R_2$, $R_3$ and $R_4$ are independently hydrogen, alkyl of 1 to 20 carbon atoms, cycloalkyl of 5 to 12 carbon atoms, phenylalkyl of 7 to 15 carbon atoms, said phenylalkyl substituted on the phenyl ring by one or two alkyl groups of 1 to 12 carbon atoms, aryl of 6 to 10 carbon atoms or said aryl substituted by one or two alkyl groups of 1 to 12 carbon atoms, or $R_3$ and $R_4$ together are straight or branched chain alkylene of 3 to 6 carbon atoms so that, with the two ring carbon atoms to which they are attached, they form a cycloalkyl ring of 5 to 6 carbon atoms, $R_5$ and $R_6$ are independently hydrogen, alkyl of 1 to 18 carbon atoms, cycloalkyl of 5 to 12 carbon atoms, phenylalkyl of 7 to 15 carbon atoms or said phenylalkyl substituted on the phenyl ring by one or two alkyl groups of 1 to 12 carbon atoms, $R_7$ is hydrogen, alkyl of 1 to 18 carbon atoms or a group of the formula —$(CH_2)_k COOR_8$ where k is 0, 1 or 2, and $R_8$ is hydrogen or alkyl of 1 to 20 carbon atoms, and when n is 2, T is a direct bond, —O—, —S—, —SO—, —SO$_2$—, —CO— or —NR— where R is alkyl of 1 to 8 carbon atoms, or when n is 2–4, T is an n-valent aliphatic hydrocarbon radical containing 1 to 20 carbon atoms, which radical is linear or branched, or which radical is interrupted by one or more moieties selected from the group consisting of —O—, —S—, —SO—, —SO$_2$—, —CO—, —NR—, phenylene and mixtures thereof, where R is alkyl of 1 to 8 carbon atoms.

Preferably, $R_1$ is the radical of formula II

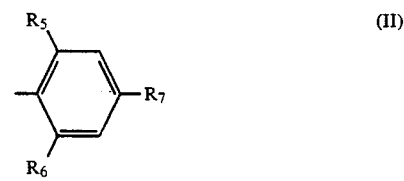

where
$R_5$, $R_6$ and $R_7$ are independently hydrogen, alkyl of 1 to 18 carbon atoms, cycloalkyl of 5 to 7 carbon atoms or phenylalkyl of 7 to 9 carbon atoms, or $R_7$ is also —$(CH_2)_k$—$COOR_8$ where k is 0, 1 or 2 and $R_8$ is alkyl of 1 to 20 carbon atoms.

Most preferably, $R_1$ is the radical of formula II where $R_5$ is hydrogen or alkyl of 1 to 8 carbon atoms, $R_6$ is alkyl of 3 to 8 carbon atoms and $R_7$ is alkyl of 3 to 8 carbon atoms or —$CH_2CH_2COOR_8$ where $R_8$ is alkyl of 1 to 18 carbon atoms.

Preferably $R_2$ is alkyl of 1 to 8 carbon atoms; most preferably alkyl of 4 to 8 carbon atoms.

Preferably $R_3$ and $R_4$ are each hydrogen.

Preferably n is 2, and T is a straight or branched alkylene of 6 to 24 carbon atoms interrupted by two or more —O— atoms, or T is a group of formula III

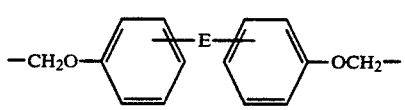

where E is a direct bond, —$CH_2$—, alkylidene of 2 to 8 carbon atoms, —O—, —S—, —SO—, —SO$_2$— or —NR—, where R is alkyl of 1 to 8 carbon atoms.

Most preferably T is alkylene of 6 to 10 carbon atoms interrupted by two or more —O— atoms, or T is a group of formula IV

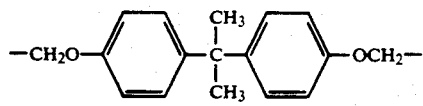

(IV)

The compounds of this invention are conveniently prepared by the reaction of an alkyl phosphorodichloridite or an aryl phosphorodichloridite with a compound having two to four beta-amino substituted alcohol groups present. These latter compounds are easily prepared by adding a substituted amine to a polyepoxide compound such as the glycidyl substituted polyols like bisphenol A or an aliphatic glycol. The phosphorodichloridites are conveniently prepared by reaction of an alcohol or phenol with phosphorus trichloride. These intermediates are largely items of commerce.

When any of R to $R_8$ or T is alkyl, such alkyl groups are, for example, methyl, ethyl, isopropyl, n-butyl, tert-butyl, tert-amyl, 2-ethylhexyl, n-octyl, tert-octyl, lauryl, n-octadecyl and eicosyl; when said radicals are cycloalkyl, they are, for example, cyclopentyl, cyclohexyl, cyclooctyl and cyclododecyl; when said radicals are phenylalkyl, they are, for example, benzyl, phenethyl, α-methylbenzyl and α,α-dimethylbenzyl; when said radicals are aryl, they are, for example, phenyl, naphthyl, or when substituted by alkyl are, for example, tolyl and xylyl; when T is alkylene interrupted by —O— groups, T is, for example, 2,5-dioxahexamethylene, 2,7-dioxaoctamethylene or 2,5,8-trioxanonamethylene.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber; and lubricating oils.

In general polymers which can be stabilized include
1. Polymers of monoolefins and diolefins, for example polyethylene (which optionally can be cross-linked), polypropylene, polyisobutylene, polybutene-1, polymethylpentene-1, polyisoprene or polybutadiene, as well as polymers of cycloolefins, for instance of cyclopenteneor norbornene.
2. Mixtures of the polymers mentioned under 1), for example mixtures of polypropylene with polyisobutylene.
3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.
4. Polystyrene, poly-(p-methylstyrene).
5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.
6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5), for instance the copolymer mixtures known as ABS-, MBS-, ASA- or AES-polymers.
7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.
8. Polymers which are derived from α,β-unsaturated acids and derivatives thereof, such as polyacrylates and polymethacrylates, polyacrylamide and polyacrylonitrile.
9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.
10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.
11. Homopolymers and copolymers of cyclic ethers, such as polyalkylene glycols, polyethylene oxide, polypropylene oxide or copolymers thereof with bis-glycidyl ethers.
12. Polyacetals, such as polyoxymethylene and those polyoxymethylenes which contain ethylene oxide as comonomer.
13. Polyphenylene oxides and sulfides, and mixtures of polyphenylene oxides with polystyrene.
14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).
15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.
17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.
18. Polycarbonates.
19. Polysulfones, polyethersulfones and polyetherketones.
20. Crosslinked polymers which are derived from aldehydes on the one hand and phenols, ureas and malamines on the other hand, such as phenol/formaldehyde resins, urea/formaldehyde resins and melamine/formaldehyde resins.
21. Drying and non-drying alkyd resins.
22. Unsaturated polyester resins which are derived from copolyesters of saturated and unsaturated dicarboxylic acids with polyhydric alcohols and vinyl compounds as crosslinking agents, and also halogen-containing modifications thereof of low flammability.
23. Thermosetting acrylic resins, derived from substituted acrylic esters, such as epoxy-acrylates, urethane-acrylates or polyester acrylates.
24. Alkyd resins, polyester resins or acrylate resins in admixture with melamine resins, urea resins, polyisocyanates or epoxide resins as crosslinking agents.
25. Crosslinked epoxide resins which are derived from polyepoxides, for example from bis-glycidyl ethers or from cycloaliphatic diepoxides.
26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.
27. Mixtures of polymers as mentioned above, for example PP/EPDM, Polyamide 6/EPDM or ABS, PVC/EVA, PVC/ABS, PVC/MBS, PC/ABS, PBTP/ABS.
28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.
29. Aqueous emulsions of natural or synthetic rubber, e.g. natural latex or latices of carboxylated styrene/butadiene copolymers.
30. Polysiloxanes such as the soft, hydrophilic polysiloxanes described, for example, in U.S. Pat. No. 4,259,467; and the hard polyorganosiloxanes described, for example, in U.S. Pat. No. 4,355,147.
31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst.
32. Radiation curable compositions containing ethylenically unsaturated monomers or oligomers and a polyunsaturated aliphatic oligomer.
33. Epoxymelamine resins such as light-stable epoxy resins crosslinked by an epoxy functional coetherified high solids melamine resin such as LSE-4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of emulsion of the stabilizer may be mixed with a solution, suspension, or emulsion of the polymer. The resulting stabilized polymer compositions of the invention may optionally also contain from about 0.01 to about 5%, preferably from about 0.025 to about 2%, and especially from about 0.1 to about 1% by weight of various conventional additives, such as the materials listed below, or mixtures thereof.

1. Antioxidants
 1.1. Alkylated monophenols, for example,
 2,6-di-tert-butyl-4-methylphenol
 2-tert.butyl-4,6-dimethylphenol
 2,6-di-tert-butyl-4-ethylphenol
 2,6-di-tert-butyl-4-n-butylphenol
 2,6-di-tert-butyl-4-i-butylphenol
 2,6-di-cyclopentyl-4-methylphenol
 2-(α-methylcyclohexyl-4,6-dimethylphenol
 2,6-di-octadecyl-4-methylphenol
 2,4,6-tri-cyclohexylphenol
 2,6-di-tert-butyl-4-methoxymethylphenol
 1.2. Alkylated hydroquinones, for example,
 2,6-di-tert-butyl-4-methoxyphenol
 2,5-di-tert-butyl-hydroquinone
 2,5-di-tert-amyl-hydroquinone
 2,6-diphenyl-4-octadecyloxyphenol
 1.3. Hydroxylated thiodiphenyl ethers, for example,
 2,2'-thio-bis-(6-tert-butyl-4-methylphenol)
 2,2'-thio-bis-(4-octylphenol)
 4,4'-thio-bis-(6-tert-butyl-3-methylphenol)
 4,4'-thio-bis-(6-tert-butyl-2-methylphenol)
 1.4. Alkylidene-bisphenols, for example,
 2,2'-methylene-bis-(6-tert-butyl-4-methylphenol)
 2,2'-methylene-bis-(6-tert-butyl-4-ethylphenol)
 2,2'-methylene-bis-[4-methyl-6-(α-methylcyclohexyl)-phenol]
 2,2'-methylene-bis-(4-methyl-6-cyclohexylphenol)
 2,2'-methylene-bis-(6-nonyl-4-methylphenol)
 2,2'-methylene-bis-[6-(α-methylbenzyl)-4-nonylphenol]
 2,2'-methylene-bis-[6-(α,α-dimethylbenzyl)-4-nonylphenol]
 2,2'-methylene-bis-(4,6-di-tert-butylphenol)
 2,2'-ethylidene-bis-(4,6-di-tert-butylphenol)
 2,2'-ethylidene-bis-(6-tert-butyl-4-isobutylphenol)
 4,4'-methylene-bis-(2,6-di-tert-butylphenol)

4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl]terephthalate.

1.5. Benzyl compounds, for example,
1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1,3,5-tris-(3,5-di-tert-butyl-4-hydroxybenzyl)isocyanurate
1,3,5-tris-(4-tert-butyl-3-hydroxy-2,6-dimethylbenzyl)isocyanurate
3,5-di-tert-butyl-4-hydroxybenzyl-phosphoric acid di-octadecyl ester
3,5-di-tert-butyl-4-hydroxybenzyl-phosphoric acid monoethyl ester, calcium-salt 1.6. Acylaminophenols, for example,
4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate 1.7. Esters of β-(3,5-di-tert-butyl-4-hydroxyphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example,
N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine 1.10 Diarylamines, for example,
diphenylamine, N-phenyl-1-naphthylamine, N-(4-tert-octylphenyl)-1-naphthylamine, 4,4'-di-tert-octyl-diphenylamine, reaction product of N-phenylbenzylamine and 2,4,4-trimethylpentene, reaction product of diphenylamine and 2,4,4-trimethylpentene, reaction product of N-phenyl-1-naphthylamine and 2,4,4-trimethylpentene.

2. UV absorbers and light stabilizers 2.1. 2-(2'-Hydroxyphenyl)-benzotriazoles, for example, the 5'-methyl-, 3',5'-di-tert-butyl-, 5'-tert-butyl-, 5'-(1,1,3,3-tetramethylbutyl)-, 5-chloro-3',5'-di-tert-butyl-, 5-chloro-3'-tert-butyl-5'-methyl-, 3'-sec-butyl-5'-tert-butyl-, 4'-octoxy, 3',5'-di-tert-amyl-, 3',5'-bis-(α,α-dimethylbenzyl), 3'-tert-butyl-5'-(2-(omega-hydroxy-octa-(ethyleneoxy)carbonyl-ethyl)-, 3'-dodecyl-5'-methyl-, and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline.

2.5. Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyl-dithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentanemethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris-(2,2,6,6-tetramethylpiperidyl)-nitrilotriacetate, tetrakis-(2,2,6,6-tetramethyl-4-piperidyl) 1,2,3,4-butanetetracarboxylate, 1,1'(1,2-ethanediyl)-bis-(3,3,5,5-tetramethylpiperazinone).

2.7. Oxalic acid diamides, for example, 4,4'-dioctyloxy-oxanilide, 2,2'-di-octyloxy-5,5'-di-tert-butyl-oxanilide, 2,2'-di-dodecyloxy-5,5'-di-tert-butyl-oxanilide, 2-ethoxy-2'-ethyl-oxanilide, N,N'-bis(3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy- as well as of o- and p-ethoxy-disubstituted oxanilides.

2.8. Hydroxyphenyl-s-triazines, for example 2,6-bis-(2,4-dimethylphenyl)-4-(2-hydroxy-4-octyloxyphenyl)-s-triazine; 2,6-bis-(2,4-dimethylphenyl)-4-(2,4-dihydroxyphenyl)-s-triazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxy-4-(2-hydroxyethoxy)-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl-4-hydroxyphenylpropionyl)hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tert-butylphenyl)pentaerythritol diphosphite, tristearyl-sorbitol triphosphite, tetrakis-(2,4-di-tert-butylphenyl) 4,4'-diphenylylenediphosphonite.

5. Compounds which destroy peroxide, for example, esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Nitrones, for example, N-benzyl-alpha-phenyl nitrone, N-ethyl-alpha-methyl nitrone, N-octyl-alpha-heptyl nitrone, N-lauryl-alpha-undecyl nitrone, N-tetradecyl-alpha-tridecyl nitrone, N-hexadecyl-alpha-pentadecyl nitrone, N-octadecyl-alpha-heptadecylnitrone, N-hexadecyl-alpha-heptadecyl nitrone, N-octadecyl-alpha-pentadecyl nitrone, N-heptadecyl-alpha-heptadecyl nitrone, N-octadecyl-alpha-hexadecyl nitrone, nitrone derived from N,N-dialkylhydroxylamine derived from hydrogenated tallow amine.

8. Polyamide stabilizers, for example copper salts in combination with iodides and/or phosphorus compounds and salts of divalent manganese.

9. Basic co-stabilizers, for example, melamine, polyvinylpyrrolidone, dicyandiamide, trially cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

10. Nucleating agents, for example, 4-tert-butyl-benzoic acid, adipic acid, diphenylacetic acid.

11. Fillers and reinforcing agents, for example, calcium carbonate, silicates, glass fibers, asbestos, talc, kaolin, mica, barium sulfate, metal oxides and hydroxides, carbon black, graphite.

12. Other additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

The phenolic antioxidant of particular interest is selected from the group consisting of n-octadecyl 3,5-di-tert-butyl-4-hydroxyhydrocinnamate, neopentanetetrayl tetrakis(3,5-di-tert-butyl-4-hydroxyhydrocinnamate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butylphenol), 1,3,5-tris(2,6-dimethyl-4-tert-butyl-3-hydroxybenzyl)isocynurate, 1,1,3,-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

A most preferred phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

The hindered amine compound of particular interest is selected from the group consisting of
bis(2,2,6,6-tetramethylpiperidin-4-yl) sebacate,
bis(1,2,2,6,6-pentamethylpiperidin-4-yl) sebacate,
di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5]decane-2,4-dione,
tris(2,2,6,6-tetramethylpiperidin-4-yl) nitrilotriacetate,
1,2-bis(2,2,6,6-tetramethyl-3-oxopiperazin-4-yl)ethane,
2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane,
tetrakis(2,2,6,6-tetramethylpiperidin-4-yl) 1,2,3,4-butanetetracarboxylate,
tetrakis(1,2,2,6,6-pentamethylpiperidin-4-yl) 1,2,3,4-butanetetracarboxylate,
polycondensation product of 2,4-dichloro-6-morpholino-s-triazine and 4,4'-hexamethylenebis(amino-2,2,6,6-tetramethylpiperidine), N,N',N",N"'-tetrakis[(4,6-bis(butyl-2,2,6,6-tetramethyl-piperidin-4-yl)-amino-s-triazin-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]undecane)diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

A most preferred hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tert-octylamino-s-triazine and 4,4'-hexamethylenebis-(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]1,10-diamino-4,7-diazadecane.

The following examples are presented for the purpose of illustration only and are not to be construed to limit the nature or scope of the instant invention in any manner whatsoever.

EXAMPLE 1

2,2-Bis[4-(2-(2,6-di-tert-butyl-4-(2-(methoxycarbonyl)ethyl)phenoxy)-3-tert-butyl-1,3,2-oxazaphospholidin-5-ylmethyloxy)phenyl]propane To a solution of 12.2 g (0.025 mole) of 2,2-bis[4-(3-tert-butylamino)-2-hydroxy-1-propoxy)phenyl]propane at −78° C. in 300 ml of methylene chloride in a 1000 ml, three-necked flask equipped with a mechanical overhead stirrer, a thermometer and an addition funnel and under a blanket of nitrogen is added dropwise a solution of 19.6 g (0.05 mole) of 2,6-di-tert-butyl-4-(2-(methoxycarbonyl)-ethyl)phenylphosphorodichlorodite and 9.1 g (0.09 mole) of triethylamine in 100 ml of methylene chloride. The reaction mixture is allowed to warm to room temperature slowly while stirring for 18 hours. The opaque while solution is concentrated under reduced pressure and then diluted with 150 ml of ethyl acetate. The solid triethylamine hydrochloride salt is removed by filtration through a pad of celite, which is washed well with additional ethyl acetate. The filtrate is concentrated again to give 28 g of a viscous oil. Purification is accomplished by medium pressure chromatography on silica gel eluting with 10% hexane in ethyl acetate. The title compound is obtained in a yield of 6.0 g (21%) as a clear viscous oil.

Analysis: Calcd for $C_{65}H_{96}N_2O_{10}P_2$: C, 69.2; H, 8.6; N, 2.5. Found: C, 69.1; H, 8.8; N, 2.3.

EXAMPLE 2

1,6-Bis[2-(2,6-di-tert-butyl-4-(2-(n-octadecyloxycarbonyl)ethyl)phenoxy)-3-tert-butyl-1,3,2-oxazaphospholidin-5-yl]-2,5-dioxahexane The general procedure of Example 1 is repeated using 2.8 g (8.3 mmol) of 2,2,15,15-tetramethyl-5,12-dihydroxy-3,14-diaza-7,10-dioxahexadecane, 10.4 g (17.5 mmol) of 2,6-di-tert-butyl-4-(2-(n-octadecyloxycarbonyl)ethyl)phenylphosphorodichlorodite, 10 ml (35 mmol) of triethylamine and 85 ml of methylene chloride to give 7.5 g of a yellow oil. Purification by chromatography (silica gel; 9/1 v/v hexane/ethyl acetate as eluent) gives 3.3 g (28% yield) of the title compound as a colorless oil.

Analysis: Calcd for $C_{86}H_{154}N_2O_{10}P_2$: C, 71.8; H, 10.8; N, 1.9. Found: C, 72.1; H, 10.9; N, 1.6.

EXAMPLE 3

Process Stabilization of Polypropylene at 536° F. (280° C.)

This example illustrates the thermal stabilizing effectiveness of the instant compounds in new technology polypropylene.

The base formulation comprises unstabilized, new technology polypropylene (PROFAX 6501, HIMONT) containing 0.1% by weight of calcium stearate. The test stabilizer is solvent blended onto polypropylene from a solution in methylene chloride. After removal of the solvent by evaporation under reduced pressure, the stabilized resin formulation is extruded at 80 rpm from a 1 inch (2.54 cm) diameter extruder at 536° F. (280° C.). The residence time in the extruder is 45 seconds.

After each of the first and fifth extrusions, the melt flow rate (in grams/10 minutes) is measured according to ASTM method D-1238 on the pellets obtained. The closer the melt flow rate after the fifth extrusion is to the melt flow rate after the first extursion the less polymer degradation has occurred. Close values would indicate superior process stabilization efficacy bestowed by the test stabilizer.

The test results are shown in the table below.

| Additive* | Additive Concentration (% by weight) | Melt Flow Rater After Extrusion | |
|---|---|---|---|
| | | 1 | 5 |
| AO A | 0.1 | 16.6 | 29.2 |
| AO A plus | 0.1 | | |
| Example 2 | 0.05 | 12.2 | 17.8 |

*AO A is neopentanetetrayl tetrakis(3,5-di-tert-butyl-4-hydroxyhydrocinnamate)

The instant compound in combination with a phenolic antioxidant provides superior process stabilization to polypropylene than does a phenolic antioxidant alone

EXAMPLE 4

Color Stabilization of Polypropylene Processed at 536° F. (280° C.)

When polypropylene is extruded as described in Example 3, resin pellets obtained after the fifth extrusion are compression molded into 125 mil (3.2 mm) thick plaquesat 380° F. (193° C.) and specimen yellowness index (YI) values are determined according to ASTM method D-1925. Low YI values indicate less yellowing and discoloration.

The results are given below.

| Additive* | Additive Concentration (% by weight) | Yellowness Index |
|---|---|---|
| AO A | 0.1 | 18.2 |
| AO A plus | 0.1 | |
| Example 2 Compound | 0.05 | 15.6 |

*AO A is neopentanetetrayl tetrakis(3,5-di-tert-butyl-4-hydroxyhydrocinnamate)

The instant compound in combination with a phenolic antioxidant protects polypropylene from discoloration better than the antioxidant when used alone.

EXAMPLE 5

When, following the general procedure of Example 3, a hindered amine compound is substituted for the phenolic antioxidant, a combination of said hindered amine compound plus instant compound provides polypropylene with effective stabilization against thermal oxidative degradation.

What is claimed is:

1. A stabilized composition which comprises (a) an organic material subject to oxidative, thermal or actinic degradation, and (b) an effective stabilizing amount of a poly-1,3,2-oxaza-phospholidine compound of formula I

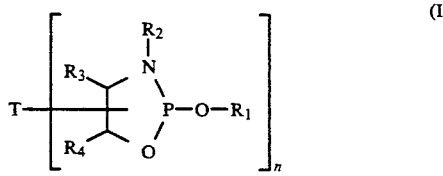

wherein n is an integer from 2 to 4, $R_1$ is alkyl of 1 to 20 carbon atoms, cycloalkyl of 5 to 12 carbon atoms, phenylalkyl of 7 to 15 carbon atoms, said phenylalkyl substituted on the phenyl ring by one or two alkyl groups of 1 to 12 carbon atoms, aryl of 6 to 10 carbon atoms or a radical of formula II

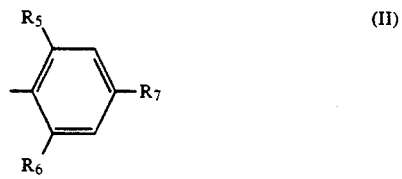

$R_2$, $R_3$ and $R_4$ are independently hydrogen, alkyl of 1 to 20 carbon atoms, cycloalkyl of 5 to 12 carbon atoms, phenylalkyl of 7 to 15 carbon atoms, said phenylalkyl substituted on the phenyl ring by one or two alkyl groups of 1 to 12 carbon atoms, aryl of 6 to 10 carbon atoms or said aryl substituted by one or two alkyl groups of 1 to 12 carbon atoms, or $R_3$ and $R_4$ together are straight or branched chain alkylene of 3 to 6 carbon atoms so that, with the two ring carbon atoms to which they are attached, they form a cycloalkyl ring of 5 to 6 carbon atoms, $R_5$ and $R_6$ are independently hydrogen, alkyl of 1 to 18 carbon atoms, cycloalkyl of 5 to 12 carbon atoms, phenylalkyl of 7 to 15 carbon atoms or said phenylalkyl substituted on the phenyl ring by one or two alkyl groups of 1 to 12 carbon atoms, $R_7$ is hydrogen, alkyl of 1 to 18 carbon atoms or a group of the formula —$(CH_2)_k COOR_8$ where k is 0, 1 or 2, and $R_8$ is hydrogen or alkyl of 1 to 20 carbon atoms, and when n is 2, T is a direct bond, —O—, —S—, —SO—, —$SO_2$—, —CO— or —NR— where R is alkyl of 1 to 8 carbon atoms, or when n is 2–4, T is an n-valent aliphatic hydrocarbon radical containing 1 to 20 carbon atoms, which radical is linear or branched, or which radical is interrupted by one or more moieties selected from the group consisting of —O—, —S—, —SO—, —$SO_2$—, —CO—, —NR—, phenylene and mixtures thereof, where R is alkyl of 1 to 8 carbon atoms.

2. A composition according to claim 1 wherein the organic material is a synthetic polymer.

3. A composition according to claim 2 wherein the polymer is a polyolefin.

4. A composition according to claim 3 wherein the polyolefin is polypropylene.

5. A composition according to claim 1 wherein the compound of component (b) is 1,6-bis[2-(2,6-di-tert-butyl-4-(2-(n-octadecyloxycarbonyl)-ethyl)phenoxy)-3-tert-butyl-1,3,2-oxazaphospholidin-5-yl]-2,5-dioxahexane.

6. A composition according to claim 1 which additionally contains an effective stabilizing amount of a phenolic antioxidant.

7. A composition according to claim 6 wherein the phenolic antioxidant is selected from the group consisting of n-octadecyl 3,5-di-tert-butyl-4-hydroxyhydrocinnamate, neopentanetetrayl tetrakis(3,5-di-tert-butyl-4-hydroxyhydrocinammate), di-n-octadecyl 3,5-di-tert-butyl-4-hydroxybenzylphosphonate, 1,3,5-tris(3,5-di-tert-butyl-4-hydroxybenzyl)isocyanurate, thiodiethylene bis(3,5-di-tert-butyl-4-hydroxyhydrocinnamate), 1,3,5-trimethyl-2,4,6-tris(3,5-di-tert-butyl-4-hydroxybenzyl)benzene, 3,6-dioxaoctamethylene bis(3-methyl-5-tert-butyl-4-hydroxyhydrocinnamate), 2,6-di-tert-butyl-p-cresol, 2,2'-ethylidene-bis(4,6-di-tert-butyl-phenol), 1,3,5-tris(2,6-dimethyl-4-tert-butyl-3-hydroxybenzyl)isocyanurate, 1,1,3-tris(2-methyl-4-hydroxy-5-tert-butylphenyl)butane, 1,3,5-tris[2-(3,5-di-tert-butyl-4-hydroxyhydrocinnamoyloxy)ethyl]isocyanurate, 3,5-di-(3,5-di-tert-butyl-4-hydroxybenzyl)mesitol, hexamethylene bis(3,5-di-tert-butyl-4-hydroxyhydrocinnamate), 1-(3,5-di-tert-butyl-4-hydroxyanilino)-3,5-di-(octylthio)-s-triazine, N,N'-hexamethylene-bis(3,5-di-tert-butyl-4-hydroxyhydrocinnamamide), calcium bis(ethyl 3,5-di-tert-butyl-4-hydroxybenzylphosphonate), ethylene bis[3,3-di(3-tert-butyl-4-hydroxyphenyl)butyrate], octyl 3,5-di-tert-butyl-4-hydroxybenzylmercaptoacetate, bis(3,5-di-tert-butyl-4-hydroxyhydrocinnamoyl)hydrazide, and N,N'-bis[2-(3,5-di-tert-butyl-4-hydroxyhydrocinnamoyloxy)-ethyl]-oxamide.

8. A composition according to claim 7 wherein the phenolic antioxidant is neopentanetetrayl tetrakis(3,5-di-tert-butyl-4-hydroxyhydrocinnamate), n-octadecyl 3,5-di-tert-butyl-4-hydroxyhydrocinnamate, 1,3,5-trimethyl-2,4,6-tris(3,5-di-tert-butyl-4-hydroxybenzyl)-benzene, 1,3,5-tris(3,5-di-tert-butyl-4-hydroxybenzyl)isocyanurate, 2,6-di-tert-butyl-p-cresol or 2,2'-ethylidene-bis(4,6-di-tert-butylphenol).

9. A composition according to claim 1 which additionally contains an effective stabilizing amount of a hindered amine compound.

10. A composition according to claim 9 wherein the hindered amine compound is selected from the group consisting of bis(2,2,6,6-tetramethylpiperidin-4-yl) sebacate,
bis(1,2,2,6,6-pentamethylpiperidin-4-yl) sebacate,
di(1,2,2,6,6-pentamethylpiperidin-4-yl) (3,5-di-tert-butyl-4-hydroxybenzyl)butylmalonate,
4-benzoyl-2,2,6,6-tetramethylpiperidine, 4-stearyloxy-2,2,6,6-tetramethylpiperidine,
3-n-octyl-7,7,9,9-tetramethyl-1,3,8-triaza-spiro[4.5]decane-2,4-dione,
tris(2,2,6,6-tetramethylpiperidin-4-yl) nitrilotriacetate, 1,2-bis(2,2,6,6-tetramethyl-3-oxopiperazin-4-yl)ethane, 2,2,4,4-tetramethyl-7-oxa-3,20-diaza-21-oxodispiro[5.1.11.2] heneicosane, polycondensation product of 2,4-dichloro-6-tert-octylamino-s-triazine and 4,4'-hexamethylenebis(amino-2,2,6,6-tetramethylpiperidine), polycondensation product of 1-(2-hydroxyethyl)-2,2,6,6-tetramethyl-4-hydroxypiperidine and succinic acid, polycondensation product of 4,4'-hexamethylenebis-(amino-2,2,6,6-tetramethylpiperidine) and 1,2-dibromoethane, tetrakis(2,2,6,6-tetramethylpiperidin-4-yl) 1,2,3,4-butanetetracarboxylate, tetrakis(1,2,2,6,6-pentamethylpiperidin-4-yl) 1,2,3,4-butanetetracarboxylate, polycondensation product of 2,4-dichloro-6-morpholino-s-triazine and 4,4'-hexamethylenebis(amino-2,2,6,6-tetramethylpiperidine), N,N',N'',N'''-tetrakis[(4,6-bis(butyl-2,2,6,6-tetramethyl-piperidin-4-yl)-amino-s-triazine-2-yl]-1,10-diamino-4,7-diazadecane, mixed [2,2,6,6-tetramethylpiperidin-4-yl/β,β,β',β'-tetramethyl-3,9-(2,4,8,10-tetraoxaspiro[5.5]undecane) diethyl]1,2,3,4-butanetetracarboxylate, mixed [1,2,2,6,6-pentamethylpiperidin-4-yl/β,β,β',β'-tetramethyl-3,9-(2,4,8,10-tetraoxaspiro[5.5]undecane)diethyl]1,2,3,4-butanetetracarboxylate, octamethylene bis(2,2,6,6-tetramethylpiperidin-4-carboxylate) and 4,4'-ethylenebis(2,2,6,6-tetramethylpiperazin-3-one).

11. A composition according to claim 10 wherein the hindered amine compound is bis(2,2,6,6-tetramethylpiperidin-4-yl) sebacate, the polycondensation product of 1-(2-hydroxyethyl)-2,2,6,6-tetramethyl-4-hydroxypiperdine and succinic acid, the polycondensation product of 2,4-dichloro-6-tetra-octylamino-s-triazine and 4,4'-hexamethylenebis(amino-2,2,6,6-tetramethylpiperidine) or N,N',N'',N'''-tetrakis[(4,6-bis(butyl-(2,2,6,6-tetramethyl-piperidin-4-yl)amino)-s-triazine-2-yl]-1,10-diamino-4,7-diazadecane.

* * * * *